US012569418B2

(12) United States Patent
Clement et al.

(10) Patent No.: US 12,569,418 B2
(45) Date of Patent: Mar. 10, 2026

(54) COSMETIC COMPOSITION COMPRISING AT LEAST ONE CLAY, AT LEAST ONE CRYSTALLIZABLE FATTY COMPOUND AND AT LEAST ONE LIPOSOLUBLE UV FILTER

(71) Applicant: L'OREAL, Paris (FR)

(72) Inventors: Franck Clement, Chevilly Larue (FR); Jean-Baptiste Boitte, Chevilly Larue (FR); Caroline Guiminot, Chevilly Larue (FR); Reda Agnaou, Chevilly Larue (FR)

(73) Assignee: L'OREAL, Paris (FR)

( * ) Notice: Subject to any disclaimer, the term of this patent is extended or adjusted under 35 U.S.C. 154(b) by 303 days.

(21) Appl. No.: 18/257,179

(22) PCT Filed: Dec. 22, 2021

(86) PCT No.: PCT/EP2021/087234

§ 371 (c)(1),
(2) Date: Jun. 13, 2023

(87) PCT Pub. No.: WO2022/136519

PCT Pub. Date: Jun. 30, 2022

(65) Prior Publication Data

US 2024/0058235 A1 Feb. 22, 2024

(30) Foreign Application Priority Data

Dec. 22, 2020 (FR) ....................................... 2013907

(51) Int. Cl.

| | |
|---|---|
| ***A61K 8/04*** | (2006.01) |
| ***A61K 8/25*** | (2006.01) |
| ***A61K 8/26*** | (2006.01) |
| ***A61K 8/35*** | (2006.01) |
| ***A61K 8/37*** | (2006.01) |
| ***A61K 8/49*** | (2006.01) |
| ***A61Q 17/04*** | (2006.01) |

(52) U.S. Cl.

CPC ................ *A61K 8/25* (2013.01); *A61K 8/042* (2013.01); *A61Q 17/04* (2013.01); *A61K 2800/40* (2013.01)

(58) Field of Classification Search

None

See application file for complete search history.

(56) References Cited

U.S. PATENT DOCUMENTS

| | | | | |
|---|---|---|---|---|
| 2003/0152531 | A1 | 8/2003 | SenGupta et al. | |
| 2004/0197279 | A1* | 10/2004 | Bleckmann ............ | A61K 8/342 424/59 |
| 2006/0280702 | A1 | 12/2006 | SenGupta et al. | |
| 2012/0183480 | A1 | 7/2012 | Nagare et al. | |
| 2013/0028852 | A1 | 1/2013 | Nagare et al. | |

FOREIGN PATENT DOCUMENTS

| | | | |
|---|---|---|---|
| EP | 3205329 | A1 | 8/2017 |
| JP | 2002121128 | A | 4/2002 |
| JP | 2002308750 | A | 10/2002 |
| JP | 2005145925 | A | 6/2005 |
| JP | 2007236176 | A | 9/2007 |
| JP | 2008543752 | A | 12/2008 |
| JP | 2010006978 | A | 1/2010 |
| JP | 2011236200 | A | 11/2011 |
| JP | 2015157781 | A | 9/2015 |
| JP | WO2014157265 | A1 | 2/2017 |
| JP | 2018104399 | A | 7/2018 |
| JP | 2019094303 | A | 6/2019 |
| JP | 2019108298 | A | 7/2019 |
| JP | 2019194175 | A | 11/2019 |

OTHER PUBLICATIONS

International Search Report and Written Opinion issued on Feb. 11, 2022 for corresponding PCT Application No. PCT/EP2021/087234.
Preliminary Search Report issued on Oct. 28, 2021 for corresponding French Application No. 2013907.
Database GNPD [Online] Mintel; Anonymous: "CC Cream 6-in-1 Tinted Moisturising Care SPF 20", Aug. 2016 XP055855327.
Database GNPD [Online] Mintel; Anonymous: "Sunscreen Light Gel SPF 50+", Jul. 2020 XP055855399.
Database GNPD [Online] Mintel; Anonymous: "Natural Face Base Tinted Moisturiser SPF 25", Apr. 2015 XP055855420.
Hongjie Cao et al.: "Enhancing Sun Care Using Bentone® Cosmetic Science Technology", 2006, pp. 1-12 XP055026631.
Database, Online, [Mintel] Anonymous: Douglas Cosmetics, "5 in 1 BB Cream," Jul. 2017 ID# 4977783.
Database, Online, [Mintel] Anonymous: Stada, "Very Hydrating Lotion for Tattooed Skin SPF 50" May 2013 ID# 2077277.

* cited by examiner

*Primary Examiner* — Brian Gulledge
(74) *Attorney, Agent, or Firm* — POLSINELLI PC

(57) ABSTRACT

The present invention concerns a composition, in particular a cosmetic composition, comprising, in a physiologically acceptable aqueous medium:
- at least one clay selected from phyllosilicates having a 2:1 layered structure,
- at least one crystallizable fat, and
- at least one liposoluble filter capable of absorbing UVA and/or UVB.

20 Claims, No Drawings

COSMETIC COMPOSITION COMPRISING AT LEAST ONE CLAY, AT LEAST ONE CRYSTALLIZABLE FATTY COMPOUND AND AT LEAST ONE LIPOSOLUBLE UV FILTER

CROSS-REFERENCE TO RELATED APPLICATIONS

This application is a national stage application (under 35 U.S.C. § 371) of PCT/EP2021/087234, filed Dec. 22, 2021, which claims benefit of French Application No. 2013907, filed Dec. 22, 2020, disclosures of both are incorporated herein by reference in their entirety.

The present invention relates to compositions, in particular cosmetic compositions, comprising, in a physiologically acceptable aqueous medium, at least one clay chosen from phyllosilicates having a 2:1 layered structure, at least one crystallizable fatty substance and at least one liposoluble filter capable of absorbing UVA and/or UVB rays.

It is known that radiation with wavelengths between 320 nm and 400 nm enables tanning of the human epidermis, while radiation with wavelengths between 280 and 320 nm, so-called UVB radiation, impairs the development of a natural tan. Exposure can also cause a detrimental change in the biomechanical properties of the epidermis, resulting in the appearance of wrinkles leading to premature ageing of the skin.

It is also known that UVA rays with a wavelength between 320 and 400 nm penetrate deeper into the skin than UVB rays. UVA rays cause an immediate and persistent darkening of the skin. Daily exposure to UVA rays, even for a short time, under normal conditions can damage collagen fibres and elastin, resulting in changes to the skin's microrelief, the appearance of wrinkles and uneven pigmentation (uneven skin tone).

To date, a wide variety of photoprotective compositions are already known to protect keratinous materials, and more particularly the skin, against the harmful effects induced by UVA and/or UVB radiation. They are usually in the form of direct or reverse emulsions in which the liquid fat phase contains the liposoluble UV filters. However, these compositions generally have uncomfortable or even unpleasant sensory aspects, including a greasy feel and a sticky skin feel, which are significant.

Consequently, there is a need for a photoprotective composition based on a liposoluble UV filter which has good cosmetic properties on application, in particular which is easy to apply, without a greasy or sticky finish on the skin, in particular after drying.

There is also a need for a photoprotective composition based on a liposoluble UV filter that limits the adhesion of particles.

There is also a need for a photoprotective composition based on a liposoluble UV filter with a sensoriality without a greasy or sticky finish on the skin while having a high level of UV protection.

The inventors have surprisingly discovered that the combination of a clay selected from phyllosilicates having a 2:1 layered structure and at least one crystallizable fat eliminates or reduces the stickiness of such a photoprotective composition, thereby limiting particle adhesion, while maintaining a high level of UVA and/or UVB protection.

More specifically, the object of the present invention is a composition, in particular a cosmetic composition, comprising, in a physiologically acceptable aqueous medium:

- at least one clay selected from phyllosilicates having a 2:1 layered structure,
- at least one crystallizable fat, and
- at least one liposoluble filter capable of absorbing UVA and/or UVB.

The present invention also relates to a method for the non-therapeutic cosmetic treatment of keratinous materials, preferably the skin, comprising the application to said keratinous materials of a composition according to the invention.

Clay Selected from Phyllosilicates Having a 2:1 Layered Structure

The composition according to the invention comprises at least one clay selected from phyllosilicates having a 2:1 layered structure. The classification of clays is referenced in the following book: Bergaya F., Lagaly G. "Handbook of Clay Science" 2nd Edition. A. Fundamentals—Elsevier Ltd, 2013.

Phyllosilicates are minerals of the silicate group constructed by stacking tetrahedral layers ("T") where the tetrahedra share three out of four vertices (the "basal" oxygens), the fourth vertex (the "apical" oxygen) being connected to an octahedral layer ("O") occupied by different cations. In phyllosilicates with a TOT structure, an octahedral O layer is interposed between two tetrahedral T layers.

The 2:1 layered structure is also called the TOT structure, where T is a tetrahedral layer and O is an octahedral layer.

Preferably, the clay is selected from smectites.

The structure of smectites differs from other phyllosilicates with a 2:1 layered structure by the presence of an interfoliar space between each TOT sheet combination which depends on the hydration state of the clay, and in which interfoliar cations are intercalated. Smectites are sometimes called "swelling" clays. Preferably, the interfoliar cations are selected from $Ca^{2+}$, $Mg^{2+}$, $Na^{+}$ and $Li^{+}$.

Preferably, the clay is selected from trioctahedral smectites.

Trioctahedral smectites are characterized by the fact that all octahedral sites in the TOT structure are mainly occupied by divalent cations. Preferably, the divalent cations of the octahedral sites are selected from $Mg^{2+}$ and $Fe^{2+}$.

In particular, the clays according to the invention are trioctahedral smectites that can be exfoliated or "activated" in the presence of water, thus forming aqueous gels due to the existence of interfoliar cations within the structure.

When water comes into contact with a clay suitable for the invention, it hydrates the layers of the clay, causing the distance between the layers to swell. Subsequently, a separation of the sheets may occur via an exfoliation and/or delamination mechanism. An aqueous gel is then obtained. Its content is essentially between 0.5% and 10% by weight, relative to the total weight of the composition, of this specific type of clay, which makes it possible to obtain gelled aqueous phases in the compositions according to the invention.

Preferably, the clay according to the invention comprises an amount by weight of $SiO_2$ greater than or equal to 30% based on the total weight of the clay, preferably between 35% and 65% by weight, and an amount by weight of MgO greater than or equal to 10%, preferably between 15% and 30% by weight.

According to a more preferred embodiment, the clay according to the invention comprises from 35% to 65% by weight of $SiO_2$, relative to the total weight of the clay, and from 15% to 30% by weight of MgO, relative to the total weight of the clay.

Preferably, in the clay according to the invention, the $SiO_2/MgO$ weight ratio is between 1 and 3, preferably between 1.5 and 2.5, preferably between 1.8 and 2.4.

Preferably, the clay according to the invention further comprises an amount by weight of $Al_2O_3$ of between 0% and 15% based on the total weight of the clay.

According to a first embodiment, a clay suitable for the invention is free of $Al_2O_3$.

According to a second embodiment, a clay suitable for the invention may comprise from 0.1% to 15% by weight of $Al_2O_3$, preferably from 8% to 12% by weight, relative to the total weight of the clay.

According to another preferred embodiment, when $Al_2O_3$ is present within the clay suitable for the invention, the $SiO_2/Al_2O_3$ weight ratio is strictly greater than 3.

Preferably, the clay according to the invention has a density of less than 2.7. Density (or specific gravity) is a very important property of minerals and is fairly simple to calculate. It is unitless, and measured using various devices and techniques that are covered in most mineralogy textbooks. Of these methods, the Jolly balance and the beam balance are the most suitable for working on mineral samples. The apparatus for making these measurements is simple and can be constructed at low cost (Sinkankas, 1966). The density is calculated as follows:

Density=(weight in air)/(weight in air−weight in water)

According to one particular embodiment, a clay suitable for the invention has the general molecular formula:

[Chem 1]

$$[M^{4+}_{8-x}M^{3+}_{x}]^{tetra}[M^{2+}_{6-y}M^{+}_{y}]^{octa}O_{20}(OH)_4\frac{X^{k+}_{x+y/}}{k}, nH_2O$$

in which $M^{4+}$ represents a cation, preferably $Si^{4+}$,
$M^{3+}$ represents a cation, preferably $Al^{3+}$,
$M^{2+}$ represents a cation, preferably $Fe^{2+}$ or $Mg^{2+}$,
$M^{+}$ represents a cation, preferably $Li^{+}$,
X represents an interfoliar cation, preferably $Ca^{2+}$, $Na^{+}$, $Li^{+}$, or mixtures thereof,
x represents the tetrahedral substitution rate,
y represents the octahedral substitution rate,
k represents the valence of the interfoliar cation X,
n represents an integer, preferably from 0 to 100.

The clay suitable for the invention is generally available in powder form.

Preferably, the clay is selected from the group consisting of hectorite, stevensite and saponite.

Advantageously, the clay is hectorite.

Hectorite can be defined by the following formula: $Na_x(Mg_{3-x}Li_x)Si_4O_{10}(OH)_2$, where x is between 0.2 and 0.4, preferably 0.3.

Preferably, the clay of the composition according to the invention is different from sauconite, sobotkite, talc and montmorillonite.

Preferably, the clay according to the invention is an unmodified clay. Unmodified clay means natural or synthetic clay that has not been modified in any way. For example, when an unmodified clay suitable for the invention is an unmodified hectorite, it is distinct from hectorites modified with a $C_{10}$ to $C_{22}$ fatty acid ammonium chloride, such as hectorite modified with distearyl dimethyl ammonium chloride. In one embodiment, an unmodified clay suitable for the invention is synthetic.

According to a preferred embodiment, an unmodified clay suitable for the invention is natural, preferably natural hectorite.

Modified clay means sheet silicates whose lipophilicity has been increased, for example by ion exchange reactions with quaternary ammonium salts, preferably quaternary ammonium chlorides. Examples of quaternary ammonium chlorides are benzyldimethylstearylammonium chloride, or quaternium-18, of the formula

[Chem 2]

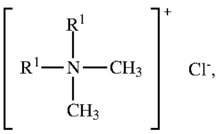

wherein the $R^1$ groups are independently selected from linear saturated C12-C20 alkyl groups. Examples of modified clays are disteardimonium hectorite or stearalkonium hectorite.

Preferably, the composition according to the invention is substantially free of modified clay, preferably substantially free of disteardimonium hectorite and stearalkonium hectorite. "Substantially free" means that the composition comprises less than 0.1% by weight of the total weight of the composition, preferably less than 0.05% by weight, preferably less than 0.01% by weight of modified clay. Preferably, the composition according to the invention is completely free of modified clay.

Preferably, the clay is present in a content of between 0.1% and 10% by weight with respect to the total weight of the composition, preferably between 0.8% and 10% by weight or between 0.5% and 5% by weight, more preferably between 1% and 3% by weight, advantageously between 1.5% and 2.5% by weight.

As an unmodified clay, and more particularly as an unmodified hectorite, the clay marketed by Elementis under the name Bentone EW or HYDROCLAY 2000 LO can be used.

Crystallizable Fat

The composition according to the invention comprises at least one crystallizable fat.

For the purposes of this invention, a crystallizable fat is understood to be a solid lipophilic compound which is deformable or non-deformable at room temperature (25° C.) and has a melting point greater than or equal to 25° C., preferably between 25° C. and 200° C., and more preferably between 25° C. and 120° C.

Some crystallizable fats are commonly called waxes.

For the purposes of the invention, the melting point is the temperature of the most endothermic peak observed in thermal analysis (DSC) as described in ISO 11357-3:1999. The melting point of the crystallizable fat can be measured using a differential scanning calorimeter (DSC), for example the calorimeter sold as MDSC 2920 by TA Instruments. Such a measurement method is for example described in PCT/EP2013/062964.

Crystallizable fats of mineral origin include: Paraffin wax, ozokerite, ceresin and microcrystalline wax.

Among crystallizable fats of vegetable origin, we can mention: Carnauba wax, candelilla wax such as that sold under the reference SP 75 G by Strahl & Pitsch, laurel wax, sugar cane wax, ceramide, esparto wax, olive wax, rice wax such as that sold under the reference NC 1720 by Cera Rica Noda, sunflower seed wax such as that sold by Koster Keunen under the reference sunflower wax hydrogenated jojoba wax, hydrogenated castor oil, hydrogenated olive oil, hydrogenated cottonseed oil, polyglyceryl-3 esters of green mimosa jojoba and sunflower waxes, and absolute flower waxes such as blackcurrant flower wax, soybean wax, myrtle fruit wax or bay leaf wax.

Crystallizable fats of animal origin include: Beeswax or modified beeswax (cerabellina), lanolin and spermaceti.

The crystallizable fat(s) may also be selected from long-chain crystallizable alcohols and mixtures thereof, such as cetearyl alcohol (C16/C18 50/50), stearyl alcohol, myristyl alcohol, cetyl alcohol, C26-C22 alcohols.

The crystallizable fat(s) may also be selected from long-chain crystallizable esters and mixtures thereof, such as the INCI compound "CETYL ESTERS (and) CETYL ESTERS MIXTURE WITH MYRISTYL STEARATE AND MYRISTYL PALMITATE", or the INCI compound "MIXTURE WITH MYRISTYL STEARATE AND MYRISTYL PALMITATE", glycol distearate, glycol stearate, cetyl palmitate such as the commercial product ERCAWAX CP V/O from the supplier ERCA, isopropyl palmitate, C20-C40 alkyl stearates, long-chain crystallizable esters of glycerol and mixtures thereof, such as the compound sold as COMPRITOL 888 CG ATO from Gattefosse (INCI: GLYCERYL DIBEHENATE (and) TRIBEHENIN (and) GLYCERYL BEHENATE) or each of its components taken separately, tricaprin, trilaurine, trimyristine, tripalmitine, tristearin, glycerol distearate, glyceryl distearate, glyceryl dipalmitostearate and linoleoyl polyoxyl-6 glyceride.

The crystallizable fat(s) may also be selected from crystallizable long-chain alkyl fatty acids and mixtures thereof, such as the INCI compound "STEARIC ACID", mixtures of stearic acid and palmitic acid, in particular from saturated C4-C28 fatty acids and unsaturated C4-C28 fatty acids.

Other crystallizable fats that can be used according to the invention include marine waxes, polyethylene waxes or polyolefin waxes in general, such as α-oligomers of olefins, e.g. Performa V® 825, 103 and 260 polymers sold by New Phase Technologies, ethylene/propylene copolymers, such as Performalene® EP 700, or Fischer-Tropsch waxes or a mixture of these products.

Preferably, the crystallizable fat is selected from crystallizable esters of C12-C24 fatty alcohols and/or crystallizable esters of C12-C24 fatty acids, and mixtures thereof, preferably selected from cetyl palmitate and a mixture of esters obtained from glycerol and behenic acid.

Preferably, the crystallizable fat is present in a content of between 0.1% and 15% by weight with respect to the total weight of the composition, preferably between 0.5% and 12% by weight, preferably between 1% and 8% by weight, advantageously between 2% and 7% by weight.

Liposoluble Filter

Among the liposoluble UV filters that can be used according to the invention, mention may be made of those selected from anthranilates; cinnamic derivatives; dibenzoylmethane derivatives; salicylic derivatives; camphor derivatives triazine derivatives such as those described in patent applications U.S. Pat. No. 4,367,390, EP863145, EP517104, EP570838, EP796851, EP775698, EP878469, EP933376, EP507691, EP507692, EP790243, EP944624 benzophenone derivatives; (3,(3-diphenylacrylate) derivatives; benzotriazole derivatives; benzalmalonate derivatives, in particular those cited in U.S. Pat. No. 5,624,663; benzimidazole derivatives; imidazolines; p-aminobenzoic acid (PABA) derivatives; benzoxazole derivatives as described in patent applications EP0832642, EP1027883, EP1300137 and DE10162844; filter polymers and filter silicones such as those described in particular in application WO-93/04665; dimers derived from a-alkylstyrene such as those described in patent application DE19855649, 4,4-diarylbutadienes such as those described in patent applications DE19755649, EP916335, EP1133980, EP1133981 and EP-A1008586 and mixtures thereof.

Examples of liposoluble organic filters are those listed above by their INCI name: Paraaminobenzoic acid derivatives: Ethyl PABA, Ethyl Dihydroxypropyl PABA, Ethylhexyl Dimethyl PABA sold as ESCALOL 507 by ISP, Salicylic derivatives: Homosalate sold as Eusolex HMS by Rona/EM Industries, Ethylhexyl Salicylate sold as NEO HELIOPAN OS by Haarmann and REIMER, TEA Salicylate, sold as NEO HELIOPAN TS by Haarmann and REIMER, Dibenzoylmethane derivatives: Butyl Methoxydibenzoylmethane sold under the trade name PARSOL 1789 by HOFFMANN LAROCHE, Isopropyl Dibenzoylmethane, Cinnamic derivatives: Ethylhexyl Methoxycinnamate sold under the trade name PARSOL MCX by HOFFMANN LAROCHE, Isopropyl Methoxy cinnamate, Isoamyl Methoxy cinnamate sold under the trade name NEO HELIOPAN E 1000 by HAARMANN and REIMER, Cinoxate, Diisopropyl Methylcinnamate, (3,(3-diphenylacrylate) derivatives: Octocrylene sold under the trade name UVINUL N539 by BASF, 50 Etocrylene, sold under the trade name UVINUL N35 by BASF, Benzophenone derivatives: Benzophenone-1 sold under the trade name UVINUL 400 by BASF, Benzophenone-2 sold under the trade name UVINUL D50 by BASF, Benzophenone-3 or Oxybenzone, sold under the trade name UVINUL M40 by BASF, Benzophenone-6 sold under the trade name Helisorb 11 by Norquay, Benzophenone-8 sold under the trade name Spectra-Sorb UV-24 by American 5 Cyanamid, Benzophenone-9 sold under the trade name UVINUL DS-49 by BASF, n-hexyl 2-(4-diethylamino-2-hydroxybenzoyl)-benzoate; Benzylidene camphor derivatives: to 3-Benzylidene camphor manufactured under the name MEXORYL SD by CHIMEX, 4-Methylbenzylidene camphor sold under the name EUSOLEX 6300 by MERCK, Triazine derivatives: Bis-Ethylhexyloxyphenol Methoxyphenyl Triazine sold under the trade name 15 TINOSORB S by CIRA GEIGY, Ethylhexyl triazone sold under the trade name UVINUL T150 by BASF, Diethylhexyl Butamido Triazone sold under the trade name UVASORB HEB by SIGMA 3V 2,4,6-tris (dineopentyl 4'-amino benzalmalonate)-s-triazine 2,4,6-tris-(diisobutyl 4'-amino benzalmalonate)-s-triazine.

Benzotriazole derivatives: Drometrizole Trisiloxane sold under the name Silatrizole by RHODIA CHIMIE, Anthranilic derivatives: Menthyl anthranilate sold under the trade name NEO HELIOPAN MA by Haarmann and REIMER, Imidazoline derivatives: Ethylhexyl Dimethoxybenzylidene Dioxoimidazoline Propionate, Benzalmalonate derivatives: Di-neopentyl 4'-methoxybenzalmalonate, Benzalmalonate-functional polyorganosiloxane such as polysilicone-15 sold under the trade name PARSOL SLX by HOFFMANN LAROCHE 4,4diarylbutadiene: 1,1-dicarboxy-(2'2'-dimethyl-propyl)-4,4diphenylbutadiene, Benzoxazole derivatives: 2,4-bis-[5-1(dimethylpropyl) benzoxazol-2-yl-(4-phenyl)-imino]-6-(2-ethylhexyl)-imino-1,3,5-triazine sold under the name Uvasorb K2A by Sigma 3V; and mixtures thereof.

Preferably, the liposoluble filter capable of absorbing UVA and/or UVB is selected from the list consisting of homosalate ethylhexyl salicylate, ethylhexyl methoxycinnamate, octocrylene butyl methoxydibenzoylmethane benzophenone-3, diethylamino hydroxybenzoyl hexyl benzoate, 4-methylbenzylidene camphor, dineopentyl 2,4,6-tris (4'-amino benzalmalonate)-s-triazine, 2,4,6-tris-(diisobutyl 4'-amino benzalmalonate)-s-triazine, bis-ethylhexyloxyphenol methoxyphenyl triazine, ethylhexyl triazone, diethylhexyl butamido triazone, drometrizole trisiloxane, polysilicon 15 di-neopentyl, 4'-methoxybenzalmalonate, 1,1-dicarboxy-(2'2'-dimethyl-propyl)-4,4-diphenylbutadiene, 2,4-bis-[5-1(dimethylpropyhbenzoxazol-2-yl-(4-phenyl)-imino]-6-(2-ethylhexyl)-imino-1,3,5-triazine, and mixtures thereof.

Even more preferably, it is selected from Homosalate Ethylhexyl Salicylate, Ethylhexyl Methoxycinnamate Octocrylene, Butyl Methoxydibenzoylmethane Ethylhexyl triazone, Bis-Ethylhexyloxyphenol Methoxyphenyl Triazine Diethylhexyl Butamido Triazone, Drometrizole Trisiloxane, and Diethylamino Hydroxybenzoyl Hexyl Benzoate.

Preferably, the liposoluble filter capable of absorbing UVA and/or UVB is present in a content of between 5% and 35% by weight relative to the total weight of the composition, preferably between 10% and 30% by weight, preferably between 12% and 25% by weight, advantageously between 15% and 23% by weight.

Water-Soluble Filter

The composition according to the invention may further comprise at least one water-soluble filter capable of absorbing UVA and/or UVB.

The water-soluble filter(s) are selected from water-soluble filters capable of absorbing UV from 320 to 400 nm (UVA), water-soluble filters capable of absorbing UV from 280 to 320 nm (UVB) and mixtures thereof.

"Water-soluble filter" means any inorganic or organic filter capable of being completely dissolved in molecular form in a liquid aqueous phase, or of being dissolved in colloidal form (e.g. in micellar form) in a liquid aqueous phase.

According to one embodiment, the composition comprises at least one water-soluble filter capable of absorbing UVA.

According to another embodiment, the composition comprises at least one water-soluble filter capable of absorbing UVB.

According to another embodiment, the composition comprises at least one water-soluble filter capable of absorbing UVB and UVA.

According to another embodiment, the composition comprises a mixture of at least one water-soluble filter capable of absorbing UVA with at least one water-soluble filter capable of absorbing UVB.

Water-Soluble Filters Capable of Absorbing UV from 320 to 400 nm (UVA)

Water-soluble filters capable of absorbing UVA include:

- Terephthalylidene Dicamphor Sulfonic Acid manufactured under the name "MEXORYL SX" by CHIMEX;
- bis-benzoazolyl derivatives as described in EP 669 323, and U.S. Pat. No. 2,463,264, and more particularly the compound Disodium Phenyl Dibenzimidazole Tetrasulfonate sold under the trade name "NEO HELIOPAN AP" by Haarmann and REIMER.

Preferably, the water-soluble filter capable of absorbing UVA is Terephthalylidene Dicamphor Sulfonic Acid.

Water-Soluble Filters Capable of Absorbing UV from 280 to 320 nm (UVB)

Water-soluble filters capable of absorbing UVB include:

- p-aminobenzoic acid (PABA) derivatives such as PABA,
- Glyceryl PABA, and
- PEG-25 PABA sold under the name "UVINUL P25" by BASF,
- Phenylbenzimidazole Sulfonic Acid sold under the trade name "EUSOLEX 232" by MERCK,
- Ferulic acid,
- Salicylic acid,
- DEA methoxycinnamate,
- Benzylidene Camphor Sulfonic Acid manufactured under the name "MEXORYL SL" by CHIMEX, and
- Camphor Benzalkonium Methosulfate manufactured under the name "MEXORYL SO" by CHIMEX.

Preferably, water-soluble filters capable of absorbing UVB are selected from Phenylbenzimidazole Sulfonic Acid, TEREPHALYLIDENE DICAMPHOR SULFONIC ACID (Mexoryl SX). Advantageously, the water-soluble filter capable of absorbing UVB is Phenylbenzimidazole Sulfonic Acid.

Mixed UVA and UVB Water-Soluble Filters

Mixed water-soluble filters capable of absorbing UVA and UVB include:

- methylene bis-benzotriazolyl tetramethylbutylphenol,
- benzophenone derivatives containing at least one sulphonic radical, such as:
  - Benzophenone-4 sold under the trade name "UVINUL MS40" by BASF,
  - Benzophenone-5, and
  - Benzophenone-9.

Preferably, the water-soluble filter capable of absorbing UVA and UVB is methylene bis-benzotriazolyl tetramethylbutylphenol.

Preferably, the at least one water-soluble filter capable of absorbing UVA and/or UVB is present in a content of between 1% and 25% by weight relative to the total weight of the composition, preferably between 2% and 10% by weight, advantageously between 3% and 8% by weight.

The presence of a water-soluble filter in the composition of the invention, if there is one, makes it possible to further improve the protection against UVA and/or UVB by ensuring that the entire surface of the skin covered by the composition is protected.

Surfactant

The composition according to the invention may further comprise at least one non-ionic surfactant.

The non-ionic surfactants which can be used in the compositions of the present invention are compounds well known to the person skilled in the art (see in particular in this respect the "Handbook of Surfactants" by M. R. Porter, published by Blackie & Son (Glasgow and London), 1991, pp. 116-178).

They are in particular selected from polyethoxylated, polypropoxylated or polyglycerolated fatty alcohols, polyethoxylated, polypropoxylated or polyglycerolated α-diols, and polyethoxylated, polypropoxylated or polyglycerolated (C1-C20)alkylphenols, the fatty chain comprising, for example, from 8 to 18 carbon atoms the number of ethylene oxide or propylene oxide groups may in particular vary from 1 to 150 and the number of glycerol groups may in particular vary from 1 to 30, C6-C30 fatty acids of polyglycerol, oxyalkylene sugar esters, C6-C30 polyethylene glycol fatty acid esters, C6-C30 sorbitan fatty acid esters, glucamine derivatives and mixtures thereof.

Other examples are condensates of ethylene oxide and propylene oxide with fatty alcohols, polyethoxylated fatty amides with preferably 1 to 100 ethylene oxide units, polyglycerol fatty amides with an average of 1 to 5 and in particular 1.5 to 4 glycerol groups, ethoxylated sorbitan fatty acid esters with 1 to 50 ethylene oxide units, sucrose fatty acid esters, polyethylene glycol fatty acid esters, alkyl polyglycosides, polyethoxylated vegetable oils preferably containing 1 to 100 ethylene oxide units, N—(C6-24-alkyl) glucamine derivatives or amine oxides, such as C10-14-alkyl amine oxides or N—(C10-14-acyl)aminopropyl morpholine oxides.

Alkyl polyglucosides can be selected, for example, from (C6-C30)alkylpolypentosides, (C6-C30)alkylpolyxylosides, (C6-C30)maltose esters, (C6-C30)sucrose esters, (C6-C30) alkyl-polyglucosides, such as decyl glucoside (C9/C11 alkyl) (1,4)polyglucoside) such as the product sold as Mydol 100 by Kao Chemicals or the product sold as Plantacare 2000 UP® by Henkel and the product sold as Oramix NS 100 by SEPPIC; caprylyl/capryl glucoside, such as the product sold as Plantacare KE 37110 by Cognis or Oramix CG 1100 by SEPPIC; lauryl glucoside, such as the product sold as Plantacare 1200 UP® by Henkel or Plantaren 1200 N® by Henkel; coconut glucoside, such as the product sold as Plantacare 818 UP® by Henkel; caprylyl glucoside, such as the product sold as Plantacare 810 UP® by Cognis; and mixtures thereof.

The surfactants may also be chosen from phospholipids, such as phosphatidic acid (phosphatidate), phosphatidylethanolamine (cephalin), phosphatidylcholine (lecithin of any origin (soya, sunflower or marine)), hydrogenated lecithin phosphatidylserine, phosphatidylinositol phosphate, phosphatidylinositol bisphosphate, phosphatidylinositol triphosphate, ceramide phosphorylcholine (Sphingomyelin), ceramide phosphorylethanolamine (Sphingomyelin) and ceramide phosphorylglycerol.

Non-ionic surfactants may also be selected from esters of citric acid and mono- and diglycerides of fatty acids, such as glycerol stearate citric ester, polysorbates, and glutamate and other amino acid derivatives such as N-stearoyl-L-glutamic acid mono-sodium salt.

The surfactants can also be selected from fermentation-derived biosurfactants, for example from rhamnolipids and sophorolipids.

Preferably, the nonionic surfactant(s) is selected from N-stearoyl-L-glutamic acid mono-sodium salt and glycerol stearate citric ester.

Alternatively or additionally, the composition of the invention may comprise at least one anionic surfactant selected from the group consisting of anionic protein derivatives of plant origin, amino acids, C6-C30 acylamino acids, phosphates and C6-C30 alkylphosphates, anionic C8-C24 alkyl polyglucosides, soaps (salts of C8-C30 fatty acids), glycinates, soybean oil derivatives, lactic acid derivatives, glycyrrhizic acids or lipopeptides, their salts and mixtures thereof, disodium cocoyl glutamate, sodium laurylsarcosinate and mixtures thereof.

When present, the nonionic surfactant(s) is (are) present in a content of between 0.05% and 20% by weight, preferably in a content of between 0.1% and 15% by weight, based on the total weight of the composition.

The presence of at least one non-ionic surfactant improves the dispersion of the solid fatty phase within the composition according to the invention.

Oil

The composition according to the invention may further comprise at least one oil.

Oil is defined as a fatty substance that is liquid at room temperature (20-25° C.) and atmospheric pressure (760 mm Hg).

Examples of oils include:

- hydrocarbon oils of vegetable origin, such as squalane, liquid triglycerides of fatty acids with 4 to 30 carbon atoms, such as heptanoic or octanoic acid triglycerides, or, for example, jojoba, babassu, sunflower, olive, coconut, brazil nut, marula, maize, soya, pumpkin, grape seed, linseed, sesame, hazelnut, apricot, macadamia, arara, coriander, castor oil, avocado, triglycerides of caprylic/capric acids such as those marketed by the company Stearineries Dubois or those marketed under the names Miglyol 810, 812 and 818 by the company Dynamit Nobel, shea butter oil;
- synthetic esters and ethers, in particular of fatty acids, such as oils of the formulae R1COOR2 and R1OR2 in which R1 represents the residue of a fatty acid or a fatty alcohol containing from 8 to 29 carbon atoms and R2 represents a hydrocarbon chain, branched or not, containing from 3 to 30 carbon atoms, such as Purcellin oil, octyl-2-dodecyl stearate, octyl-2-dodecyl erucate, isostearyl isostearate; hydroxylated esters such as isostearyl lactate, octylhydroxystearate, octyldodecyl hydroxy stearate, diisostearyl malate, triisocetyl citrate, fatty alcohol decanoates, heptanoates, octanoates; polyol esters, such as propylene glycol dioctanoate, neopentyl glycol diheptanoate and diethylene glycol diisononanoate; and pentaerythritol esters such as pentaerythryl tetraisostearate;
- linear or branched hydrocarbons, of mineral or synthetic origin, volatile or non-volatile, and their derivatives, such as branched alkanes with 8 to 18 carbon atoms, for example C8-C18 iso-alkanes (also called isoparaffins) such as isododecane, isodecane, isohexadecane, such as the isoparaffins sold under the trade names Isopar by the company Exxon Chemical or the oils sold under the trade names Permethyl by the company Presperse, isohexadecane and isododecane marketed by the company INEOS; as well as petroleum jelly and hydrogenated polyisobutene such as Parleam® oil; volatile linear alkanes comprising from 7 to 17 carbon atoms such as undecane, tridecane;
- fatty alcohols liquid at room temperature with 8 to 26 carbon atoms, such as octyldodecanol, 2-butyloctanol, 2-hexyldecanol, 2-undecylpentadecanol or oleic alcohol; and
- mixtures thereof.

In particular, the following oils can be mentioned:

- esters resulting from the reaction of at least one fatty acid containing at least 6 carbon atoms, preferably from 6 to 26 carbon atoms and better still from 6 to 20 carbon atoms, and even better still from 6 to 16 carbon atoms and at least one alcohol containing from 1 to 17 carbon atoms and better still from 3 to 15 carbon atoms; particular mention may be made of isopropyl myristate, isopropyl palmitate, ethyl 2-hexyl caprate/caprylate (or octyl caprate/caprylate), ethyl 2-hexyl palmitate, isostearyl neopentanoate, isononyl isonanoate hexyl laurate, esters of lactic acid and fatty alcohols containing 12 or 13 carbon atoms, dicaprylyl carbonate such as that marketed under the name CETIOL CC by the company COGNIS,
- fatty acid ethers containing 6 to 20 carbon atoms, such as dicaprylyl ether (Cetiol OE from Cognis), —glycerol ethers containing 6 to 12 carbon atoms, such as 2-ethylhexylglycerol ether (INCI name: ethylhexylglycerin), such as Sensiva SC 50 from Schulke & Mayr GmbH;
- octydodecanol,
- alkanes such as those described in Cognis patent applications WO 2007/068371, or WO2008/155059 (mixtures of distinct alkanes differing by at least one carbon). These alkanes are obtained from fatty alcohols, which in turn are obtained from coconut or palm oil.

Examples of linear alkanes suitable for the invention are n-heptane (C7), n-octane (C8), n-nonane (C9), n-decane (C10), n-undecane (C11), n-dodecane (C12), n-tridecane (C13), n-tetradecane (C14) and mixtures thereof. According to one particular embodiment, the volatile linear alkane is selected from n-nonane, n-undecane, n-dodecane, n-tridecane, n-tetradecane, and mixtures thereof.

According to a preferred embodiment, one may mention the mixtures of n-undecane (C11) and n-tridecane (C13) obtained in examples 1 and 2 of the application WO2008/155059 to the company Cognis;

polyesters obtained by condensation of dimer and/or trimer of unsaturated fatty acid and diol, such as the polyesters of dilinoleic acid and diol marketed by Biosynthis under the name Viscoplast and in particular the polymer bearing the INCI name dilinoleic acid/propanediol copolymer; and mixtures thereof.

Preferably, the oil(s) are selected from dicaprylyl carbonate and dicaprylyl ether.

When present, the oil(s) is (are) present at a content of between 0.1% and 20% by weight, preferably in a content of between 0.5% and 10% by weight, relative to the total weight of the composition.

The presence of at least one oil further enhances the sensoriality of the composition of the invention.

Aqueous Phase

The composition according to the invention comprises a physiologically acceptable aqueous medium.

Preferably, the composition according to the invention comprises an aqueous medium comprising at least water.

The aqueous medium may comprise at least one other water-soluble organic solvent, at 25° C., selected for example from:

C1-C4 monoalkanols. A "$C_1$-$C_4$ monoalkanol" is any saturated, linear or branched alkane compound having from 1 to 4 carbon atoms and a single hydroxyl function (OH). The $C_1$-$C_4$ monoalkanol(s) present in the compositions of the invention may be selected from methanol, ethanol, propanol, isopropanol, butanol or mixtures thereof, polyols having in particular 2 to 20 carbon atoms, preferably 2 to 6 carbon atoms, such as glycerol, diglycerol, propylene glycol, isoprene glycol, dipropylene glycol, butylene glycol, hexylene glycol, 1,3-propanediol, 1,2-octanediol, pentylene glycol, simple sugars, water-soluble polyalkylene glycols; and mixtures thereof.

Preferably, the other water-soluble organic solvent(s) are selected from the list consisting of 1,2-octanediol, ethanol and glycerol.

They are generally present in concentrations ranging from 0.2% to 50% by weight, more preferably from 0.5 to 30%, and most preferably from 1% to 10% by weight with respect to the total weight of the composition.

Composition

Preferably, the composition according to the invention is an aqueous gel.

Preferably, the composition according to the invention comprises a solid fatty phase dispersed in an aqueous phase, the solid fatty phase comprising the crystallizable fat(s) and the liposoluble UV filter(s). Preferably, the liposoluble UV filter(s) are encapsulated in the particles of the crystallizable fat(s).

These particles are generally referred to as solid lipid nanoparticles (SLN). These lipid particles consist of a lipid matrix solid at room temperature, or a matrix formed by a mixture of liquid lipids (oils) and solid at room temperature, optionally encapsulating at least one liposoluble compound.

These lipid particles can be dispersed in an aqueous medium, so that it is possible to speak of a solid/liquid dispersion. The lipid particles are advantageously stabilized in the suspension by at least one surfactant.

Preferably, the solid fatty phase of the composition of the invention is in the form of substantially spherical particles with a number average diameter of between 200 nm and 100 µm, preferably between 200 nm and 10 µm.

In addition, the composition according to the invention may comprise one or more conventional cosmetic adjuvants chosen in particular from fats; thickeners such as sodium alginate, carrageenans, xanthans, scleroglucan, cellulose or its derivatives; softeners; antioxidants; active ingredients; stabilisers; sequestrants; anti-foaming agents; moisturisers; vitamins; perfumes; preservatives; fillers; or any other ingredient usually used in cosmetics and/or dermatology, in particular for the manufacture of compositions in the form of aqueous gels.

Fillers

The fillers that may be included in the composition according to the invention are colourless or white, solid particles of any shape, which are in an insoluble form and dispersed in the medium of the composition. Mineral or organic, natural or synthetic, they allow the composition to be given softness, mattness and uniformity. In addition, these fillers have the advantage of combating various aggressions such as sebum or sweat.

Examples of these fillers are talc, mica, silica, kaolin, polyalanine and polyethylene powders, tetrafluoroethylene polymer powders (Teflon®), lauroyl-lysine, starch, boron nitride, hollow polymeric microspheres such as polyvinylidene chloride/acrylonitrile microspheres like Expancel® (Nobel Industrie), acrylic acid copolymers, silicone resin microbeads (e.g. Tospearls® from Toshiba), elastomeric polyorganosiloxane particles, precipitated calcium carbonate, magnesium carbonate and magnesium hydrocarbonate, hydroxyapatite, barium sulphate, polyurethane powders, composite fillers, hollow silica microspheres, and glass or ceramic microcapsules. Alternatively, particles, which are in the form of hollow sphere portions, as described in patent applications JP-2003 128 788 and JP-2000 191 789, may be used.

In particular, such fillers may be present in a composition according to the invention in a content of between 0.01% and 25% by weight, in particular between 0.1% and 20% by weight, in particular between 1% and 10% by weight, relative to the total weight of the composition The terms "between . . . and . . . ", "from . . . to . . . " and "varies from . . . to . . . " shall be understood to include the low and high figures, unless otherwise specified.

Concrete, but by no means limiting, examples illustrating the invention will now be given.

In the examples, the pressure is atmospheric pressure unless otherwise stated.

EXAMPLES

Example 1: Preparation of the Compositions According to the Invention C1, C2 and C3 and the Comparative Compositions C4*, C5*, C6* and C7*

The compositions according to the invention C1, C2 and C3 and the comparative compositions C4*, C5*, C6* and C7* are prepared with the ingredients mentioned in the table below, according to the following protocol:

The crystallizable fat is melted at 80° C., and liquid oil is added if necessary. The liposoluble UV filter(s) is (are) added to the molten crystallizable fat while hot. This fatty phase is emulsified with a hot aqueous phase containing the surfactant(s), the clay, and the water-soluble filter(s) if any. The resulting emulsion is stirred for 15 minutes and then cooled from 80° C. to 40° C. During this cooling, other ingredients such as fillers and preservatives are added. A vacuum is created to remove air bubbles from the composition. An aqueous gel is obtained, comprising a crystallizable fat dispersion encapsulating the liposoluble UV filter(s).

The quantities of each ingredient are expressed as a ratio by mass to the total weight of the composition.

The comparative composition C7* comprises at least one liposoluble filter, but does not comprise clay or a crystallizable fat.

Example 2: Anti-Adhesion Test of Compositions C1, C2 and C3 According to the Invention and of Comparative Compositions C4*, C5*, C6* and C7*

The non-stickiness of the compositions C1, C2 and C3 according to the invention and of the comparative compositions C4*, C5*, C6* and C7* was evaluated according to the following protocol:

Bioskin plates (reference: MAPREKOS Bioskin K520 or K531 plate A4 smooth and flat surface thickness 2 mm

TABLE 1

| Ingredient | C1 (% w/w) (invention) | C2 (% w/w) (invention) | C3 (% w/w) (invention) | C4* (% w/w) (comparative) | C5* (% w/w) (comparative) | C6* (% w/w) (comparative) | C7* (% w/w) (comparative) |
|---|---|---|---|---|---|---|---|
| Water | Qsp 100 | Qsp 100 | Qsp 100 | Qsp 100 | Qsp 100 | Qsp 100 | Qsp 100 |
| Sodium alginate | 0.7 | 0.7 | 0.7 | 0.7 | — | — | — |
| 2-ethylhexyl salicylate (INCI: ETHYLHEXYL SALICYLATE) | 8 | 8 | 8 | 8 | 8 | 8 | 8 |
| Glycerol stearate citric ester (INCI: GLYCERYL STEARATE CITRATE) | 2.2 | 2.2 | 2.2 | 2.2 | 2.2 | 2.2 | 2.2 |
| 2-phenyl-1H-benzimidazole-5-sulphonic acid (INCI: PHENYLBENZIMIDAZOLE SULFONIC ACID) | — | — | 4 | 4 | 4 | 4 | 4 |
| Stabilized dioctyl carbonate (INCI: DICAPRYLYL CARBONATE) | 1 | 1 | 1 | 15 | 1 | 1 | 15 |
| Preservative | Qs | Qs | Qs | Qs | Qs | Qs | Qs |
| N-stearoyl-L-glutamic acid mono-sodium salt (INCI: SODIUM STEAROYL GLUTAMATE) | 2 | 2 | 2 | 2 | 2 | 2 | 2 |
| 1-[4-(1,1-dimethylethyl)phenyl]-3-(4-methoxyphenyl)propane-1,3-dione (INCI: BUTYL METHOXYDIBENZOYL METHANE) | 8 | 8 | 8 | 8 | 8 | 8 | 8 |
| Unmodified hectorite (HYDROCLAY 2000 LO/ELEMENTIS) | 2 | 2 | 2 | 2 | — | — | — |
| Xanthan gum (INCI: XANTHAN GUM) | — | — | — | — | 0.8 | 0.8 | 0.8 |
| Mixture of mono-, di-, triglycerides of behenic acid (INCI: GLYCERYL DIBEHENATE (and) TRIBEHENIN (and) GLYCERYL BEHENATE) | 3 | — | 3 | — | 3 | — | — |
| Glycerine | — | — | — | — | 1 | 1 | 1 |
| Cetyl Palmitate (INCI: CETYL PALMITATE) | — | 3 | — | — | — | 3 | — |

The comparative composition C4* contains an unmodified clay, at least one liposoluble filter but no crystallizable fat.

The comparative composition C5* comprises at least one liposoluble filter, at least one crystallizable fat but does not comprise clay.

The comparative composition C6* does not comprise clay, but comprises at least one liposoluble filter and a crystallizable fat different from that in the comparative composition C5*.

cut in squares 5*5 cm) are rinsed with a detergent solution (micellar solution, surfactant solution) and then with water and left to dry for 2 hours in an oven at 40° C.

40 to 60 mg of each composition are applied to a Bioskin plate. Spreading is done according to the following procedure: the formula is first spread with a finger pad using right-to-left movements (5 round trips), then the plate is turned by ¼ turn and 5 round trips are repeated. The operation is repeated on all 4 sides of the plate.

The plates are weighed to ensure that they contain at least 30 mg of composition.

Each plate is left to dry for at least 20 minutes on a hot plate (reference: EKIUM PCMF 400*600).

hydrophobic black iron oxide (FeO) particles are applied using a sieve to even out the particle size, the amount of particles is measured accurately using a precision balance. The plate is left to rest for 15 minutes to allow the particles to adhere.

the plate is then placed on a rotating support, a flow of air is then turned on for 5 seconds using a compressor set at 0.2 bar (reference: Compressors Smart Jet Pro 875 by IWATA) and an airbrush positioned at 30 cm from the plate (reference: Aerograf IWATA HP-G5 (0.5 mm) in such a way that the sample is swept by this flow transversely.

The plate is then weighed again to identify the amount of particles that have adhered to the formula film.

A composition is considered to be non-sticky when the percentage of FeO removed when the Skin FX support passes through the airflow is greater than or equal to 70%.

The results of this test are presented in the following table:

TABLE 2

| Composition | Amount of FeO deposited (mg) | Amount of FeO remaining after passing through an airflow (mg) | Percentage of FeO removed by the airflow |
|---|---|---|---|
| C1 | 30.3 | 8.1 | 74% |
| C2 | 66.2 | 12.8 | 80.5% |
| C3 | 38.1 | 5.4 | 85.8% |
| C4* | 51.1 | 43 | 15.8% |
| C5* | 24.1 | 8.5 | 48.2% |
| C6* | 44.6 | 31.7 | 28.9% |
| C7* | 73.8 | 54.9 | 25% |

When the compositions do not contain unmodified clay and/or crystallizable fats (comparative compositions C4*, C5*, C6* and C7*), iron oxide adhesion is important because the compositions are sticky. Only the compositions according to the invention comprising the combination of an unmodified clay and a crystallizable fat (compositions C1, C2 and C3) make it possible to obtain non-sticky compositions.

Example 3: Other Compositions According to the Invention and Comparison

A further composition according to the invention C8 and a further comparative composition C9* were prepared according to the following protocol:

1) The fatty phase, containing the crystallizable fats as well as the liposoluble filters and a first surfactant, is introduced into the tank and heated to 80° C. (emulsifier speed at 400 rpm with 20 rpm scraping).
2) When all the solid raw materials are melted, the clay or gellan gum is added to be dispersed in this fatty phase (emulsifier speed at 400 rpm; coaxial 90 rpm; scraper 50 rpm).
3) The aqueous phase containing the second surfactant, water-soluble filters and water is prepared separately and heated to 80° C. in a 5 L Maxilab tank (Olsa brand).
4) The aqueous phase is added to the fatty phase (emulsifier speed at 4000 rpm; coaxial 150 rpm; scraper 75 rpm). After 15 min, sodium alginate, when present, is added (emulsifier speed 4000 rpm; coaxial 150 rpm; scraper 75 rpm).
5) After 10 min, the heating is stopped and cooled to a setpoint emperature of 10° C. At the same time, the charge is introduced into the mixture (emulsifier speed 2000 rpm; coaxial 150 rpm; scraper 75 rpm).
6) At 40° C., the preservative and antioxidant are added, at 30° C. the rest of the preservatives are added.
7) If necessary, the pH is adjusted according to the hydrophilic UV filters used.

The SPF index of the compositions was determined according to the ISO 24442 method.

TABLE 3

| Ingredient | C8 (% w/w) (invention) | C9* (% w/w) (comparative) |
|---|---|---|
| Water | Qsp 100 | Qsp 100 |
| Glycerol stearate citric ester (INCI: GLYCERYL STEARATE CITRATE) | 3.00 | 3.00 |
| Cellulose | 0.80 | 0.80 |
| 2-phenyl-1H-benzimidazole-5-sulphonic acid (INCI: PHENYLBENZIMIDAZOLE SULFONIC ACID) | 2.50 | 2.50 |
| Caprylyl glycol | 3.00 | 3.00 |
| Ethylhexyl triazone | 3.00 | 3.00 |
| Mixture of mono-, di-, triglycerides of behenic acid (INCI: GLYCERYL DIBEHENATE (and) TRIBEHENIN (and) GLYCERYL BEHENATE) | 3.00 | 3.00 |
| 1-[4-(1,1-dimethylethyl)phenyl]-3-(4-methoxyphenyl)propane-1,3-dione (INCI: BUTYL METHOXYDIBENZOYL-METHANE) | 3.00 | 3.00 |
| L-Arginine | 1.00 | 1.00 |
| (E-E)-3,3'-(1,4-phenylenedimethylidene)-bis(2-oxobornane-10-sulfonic acid) in 32% aqueous solution (INCI: TEREPHTHALYDENE DICAMPHOR SULFONIC ACID) | 3.00 | 3.00 |
| Phenol, 2,2'-[6-(4-methoxyphenyl)1,3,5-triazine-2,4-diyl]bis[5[(2-ethylhexyl)oxy] (INCI: BIS-ETHYLHEXYLOXYPHENOL-METHOXYPHENYL TRIAZINE) | 4.50 | 4.50 |
| Homomenthyl salicylate (INCI: HOMOSALATE) | 3.00 | 3.00 |
| Glycerine | 4.66 | 4.66 |
| Gellan gum (INCI: GELLAN GUM) | — | 1.00 |
| Cetyl Palmitate (INCI: CETYL PALMITATE) | 3.00 | 3.00 |
| Stabilized dioctyl ether (INCI: DICAPRYLYL ETHER) | 6.00 | 6.00 |
| Titanium dioxide | 2.00 | 2.00 |
| 2-ethylhexyl salicylate (INCI: ETHYL-HEXYLSALICYLATE) | 4.00 | 4.00 |
| N-stearoyl-L-glutamic acid mono-sodium salt (INCI: SODIUM STEAROYL GLUTAMATE) | 2.00 | 2.00 |
| Salicylic acid | 0.30 | 0.30 |
| Unmodified hectorite (HYDROCLAY 2000 LO/ELEMENTIS) | 2.00 | — |
| Sodium alginate | 0.90 | — |
| SPF Index | 48.5 | 48.3 |

Composition C8 according to the invention has better cosmeticity, particularly in terms of stickiness, than the comparative composition C9* which does not contain hectorite, while having a sun protection factor of the same order of magnitude. These results show that the presence of a clay chosen from among the phyllosilicates having a 2:1 layered structure in the compositions of the invention makes it possible to improve their cosmeticity without altering their performance in terms of sun protection.

Example 4: Other Compositions According to the Invention

Other compositions C10, C11 and C12 according to the invention have been prepared with the ingredients listed in the table below and according to the protocol described in example 1.

| Ingredient | C10 (% w/w) (invention) | C11 (% w/w) (invention) | C12 (% w/w) (invention) |
|---|---|---|---|
| Water | Qsp 100 | Qsp 100 | Qsp 100 |
| Sodium alginate | 0.7 | 0.7 | 0.7 |
| 2-ethylhexyl salicylate (INCI: ETHYLHEXYL SALICYLATE) | 8 | 8 | 8 |
| Glycerol stearate citric ester (INCI: GLYCERYL STEARATE CITRATE) | 2.2 | 2.2 | 2.2 |
| Stabilized dioctyl carbonate (INCI: DICAPRYLYL CARBONATE) | 1 | 1 | 1 |
| Preservative | Qs | Qs | Qs |
| N-stearoyl-L-glutamic acid mono-sodiumsalt (INCI: SODIUM STEAROYL GLUTAMATE) | 2 | 2 | 2 |
| 1-[4-(1,1-dimethylethyl)phenyl]-3-(4-methoxyphenyl)propane-1,3-dione (INCI: BUTYL METHOXYDI-BENZOYLMETHANE) | 8 | 8 | 8 |
| Unmodified hectorite (HYDROCLAY 2000 LO/ELEMENTIS) | 0.1 | 0.5 | 0.8 |
| Mixture of mono-, di-, triglycerides of behenic acid (INCI: GLYCERYL DIBEHENATE (and) TRIBEHENIN (and) GLYCERYL BEHENATE) | 3 | 3 | 3 |

The non-stickiness of the compositions C1, C2 and C3 according to the invention was evaluated according to the protocol of example 2. The results are gathered in the Table below.

| Composition | Amount of FeO deposited (mg) | Amount of FeO remaining after passing through an airflow (mg) | Percentage of FeO removed by the airflow |
|---|---|---|---|
| C10 | 31.4 | 14.9 | 52.5% |
| C11 | 37.6 | 17.2 | 54.2% |
| C12 | 52.6 | 17.8 | 66.2% |

The compositions according to the invention comprising the combination of an unmodified clay and a crystallizable fat (compositions C10 to C12) make it possible to obtain non-sticky compositions.

The invention claimed is:

1. A composition comprising, in a physiologically acceptable aqueous medium:

at least one clay selected from phyllosilicates having a 2:1 layered structure, at least one crystallizable fat, and at least one liposoluble filter capable of absorbing UVA and/or UVB, wherein the clay is present in a content of between 0.8% and 10% by weight relative to the total weight of the composition.

2. The composition according to claim 1, wherein the clay is selected from smectites.

3. The composition according to claim 1, wherein the clay is selected from the group consisting of hectorite, stevensite and saponite.

4. The composition according to claim 1, wherein the clay is present in a content of between 0.8% and 5% by weight relative to the total weight of the composition.

5. The composition according to claim 1, wherein the crystallizable fat is selected from crystallizable esters of C12-C24 fatty alcohols and/or crystallizable esters of C12-C24 fatty acids, and mixtures thereof.

6. The composition according to claim 1, wherein the crystallizable fat is present in a content of between 0.1% and 15% by weight relative to the total weight of the composition.

7. The composition according to claim 1, wherein the liposoluble filter capable of absorbing UVA and/or UVB is selected from homosalate ethylhexyl salicylate, ethylhexyl methoxycinnamate, octocrylene butyl methoxydibenzoylmethane benzophenone-3, diethylamino hydroxybenzoyl hexyl benzoate, 4-methylbenzylidene camphor, dineopentyl 2,4,6-tris(4'-amino benzalmalonate)-s-triazine, 2,4,6-tris-(diisobutyl 4'-amino benzalmalonate)-s-triazine, bis-ethylhexyloxyphenol methoxyphenyl triazine, ethylhexyl triazone, diethylhexyl butamido triazone, drometrizole trisiloxane, polysilicon 15 di-neopentyl, 4'-methoxybenzalmalonate, 1,1-dicarboxy-(2'2'-dimethyl-propyl)-4,4-diphenylbutadiene, 2,4-bis-[5-1 (dimethylpropyl)benzoxazol-2-yl-(4-phenyl)-imino]-6-(2-ethylhexyl)-imino-1,3,5-triazine, and mixtures thereof.

8. The composition according to claim 1, wherein the liposoluble filter capable of absorbing UVA and/or UVB is present in a content of between 5% and 35% by weight relative to the total weight of the composition.

9. The composition according to claim 1, further comprising at least one water-soluble filter capable of absorbing UVA and/or UVB.

10. The composition according to claim 9, wherein the at least one water-soluble filter capable of absorbing UVA and/or UVB is present in a content of between 1% and 25% by weight relative to the total weight of the composition.

11. The composition according to claim 1, further comprising at least one nonionic surfactant.

12. The composition according to claim 1, further comprising at least one oil.

13. The composition according to claim 1, being an aqueous gel.

14. The composition according to claim 1, wherein the clay is unmodified.

15. The composition according to claim 1, wherein the clay is selected from trioctahedral smectites.

16. The composition according to claim 1, wherein the crystallizable fat is selected from cetyl palmitate and a mixture of esters obtained from glycerol and behenic acid.

17. The composition according to claim 2, wherein the clay is present in a content of between 0.8% and 5% by weight relative to the total weight of the composition.

18. The composition according to claim 3, wherein the clay is present in a content of between 0.8% and 5% by weight relative to the total weight of the composition.

19. The composition according to claim 2, wherein the crystallizable fat is selected from crystallizable esters of C12-C24 fatty alcohols and/or crystallizable esters of C12-C24 fatty acids, and mixtures thereof.

20. The composition according to claim 3, wherein the crystallizable fat is selected from crystallizable esters of C12-C24 fatty alcohols and/or crystallizable esters of C12-C24 fatty acids, and mixtures thereof.

* * * * *